United States Patent [19]

Screws et al.

[11] Patent Number: 5,707,858
[45] Date of Patent: Jan. 13, 1998

[54] PROCESS FOR THE TREATMENT OF CELLULOSIC FABRICS WITH CELLULASES

[75] Inventors: Garrett A. Screws, Danbury, Conn.; Gitte Pedersen, Frederiksberg C., Denmark

[73] Assignee: Novo Nordisk A/S, Bagsvaerd, Denmark

[21] Appl. No.: 446,670

[22] PCT Filed: Nov. 30, 1993

[86] PCT No.: PCT/US93/11629

§ 371 Date: Jun. 15, 1995

§ 102(e) Date: Jun. 15, 1995

[87] PCT Pub. No.: WO94/12578

PCT Pub. Date: Jun. 9, 1994

Related U.S. Application Data

[63] Continuation of Ser. No. 982,927, Nov. 30, 1992, abandoned.

[51] Int. Cl.$^6$ .......... D06M 16/00; D06M 11/00; C12N 9/42; C09B 67/00
[52] U.S. Cl. .......... 435/263; 8/116.1; 8/401; 435/209
[58] Field of Search .......... 435/263, 69.1, 435/70.1, 209; 536/41; 8/401, 116.1

[56] References Cited

U.S. PATENT DOCUMENTS

| | | | |
|---|---|---|---|
| 4,912,056 | 3/1990 | Olson | 435/263 |
| 5,232,851 | 8/1993 | Cox et al. | 435/263 |
| 5,246,853 | 9/1993 | Clarkson et al. | 435/263 |

FOREIGN PATENT DOCUMENTS

| | | |
|---|---|---|
| 8909259 | 10/1989 | WIPO . |
| 9117243 | 11/1991 | WIPO . |
| 9206183 | 4/1992 | WIPO . |

OTHER PUBLICATIONS

Selby et al. "The Degradation of Cotton Cellulose by The Extracellular Cellulase of *Myrothecium verrucarra*" Biochem J. 88 288–296 1963.

*Primary Examiner*—Nancy Degen
*Attorney, Agent, or Firm*—Steve T. Zelson, Esq.; Elias J. Lambiris, Esq.

[57] ABSTRACT

This invention relates to an improved cellulase treatment of cellulosic fabrics to improve fabric quality with respect to handle and appearance without loss of fabric wettability. Cellulosic fabrics are subjected to two treatments with cellulase. The resulting fabric has a soft and smooth feel and reduced pilling.

29 Claims, No Drawings

PROCESS FOR THE TREATMENT OF CELLULOSIC FABRICS WITH CELLULASES

This application is a 371 of PCT/US93/11629, filed on Nov. 30, 1993, which is a continuation of U.S. Ser. No. 07/982,927, filed on Nov. 30, 1992, now abandoned.

FIELD OF THE INVENTION

This invention relates to an improved cellulase treatment of cellulosic fabrics to improve fabric quality with respect to handle and appearance without loss of fabric wettability.

BACKGROUND OF THE INVENTION

Most newly manufactured cotton fabrics and cotton blend fabrics have a handle that is rather hard and stiff unless they are treated with finishing components. Furthermore, the fabric surface is not smooth due to small fuzzy fibers protruding from it. In addition, after a relatively short period of wear, pilling appears on the fabric surface thereby giving it an unappealing, worn look.

A high degree of fabric softness and smoothness can be obtained by using fine, i.e., low-denier, yarns in weaving. However, the resulting cost is high as the loom output decreases concurrently with the weft yarn diameter.

A less expensive way of ensuring a soft and smooth fabric "handle" is to impregnate the finished fabric with a softening agent, typically a cationic, sometimes silicone-based, surface active compound. However, this treatment does not remove pills and fuzz. Furthermore, the fabric obtains a somewhat greasy "handle" and is not wash-proof, and its moisture absorbency is often considerably reduced.

Another known method for obtaining a soft and smooth fabric is treating cellulosic fabrics with cellulases. See Bazin et al., "Enzymatic Bio-Polishing of Cellulosic Fabric," presented at the 58th Congress of the Association of Chemists and the Textile Industry in Mulhouse, France (Oct. 25, 1991) and Asferg et al., "Softening and polishing of cotton fabrics by cellulase treatment," ITB Dyeing/Printing/Finishing (Feb. 1990).

Cellulase treatment of the fabric surface improves fabric quality with respect to handle and appearance without loss of fabric wettability. The most important effects are less fuzz and pilling, increased gloss/luster, improved fabric handle, increased durable softness and improved water absorbency. These effects are referred to as Bio-Polishing effects. Presently, cellulases are applied in a single dose.

One disadvantage of enzymatic treatment of cellulosic fabrics has been that the large dose amounts needed to achieve Bio-Polishing effects in the finishing step causes "yellowing" of the fabric during drying.

It is an object of the present invention to provide an improved enzymatic process for treating cellulosic fabrics to achieve Bio-Polishing effects.

It is also an object of the present invention to overcome the yellowing problem of the present enzymatic processes for treating cellulosic fabrics.

SUMMARY OF THE INVENTION

The present invention is directed to a multiple step cellulosic treatment of a cellulase fabric in order to achieve improved Bio-Polishing effects.

DETAILED DISCLOSURE OF THE INVENTION

The present invention is directed to a process for treating a cellulosic fabric comprising applying at least two cellulase treatments to the fabric in order to achieve Bio-Polishing effects. The process according to the present invention is especially useful in continuous textile manufacturing processes. However, the process may also be used in batch operations.

The initial enzymatic treatment should result in a weight loss between about 0.05 and about 10.0%, preferably between about 0.5 and about 8.0%, and most preferably between about 1.0 and about 5.0%, of the weight of the cellulosic fabric. Weight loss is defined herein as the weight loss caused solely by the cellulase treatment, i.e., the weight loss caused by any mechanical treatment during the cellulase treatment, e.g., washing, tumbling, stretching, pulling, etc., is not taken into account.

The weight loss in the first step can be achieved by a dosage of between about 100 and about 40,000 EGU/kg of fabric, preferably between about 200 and 20,000 EGU/kg of fabric. The enzyme activity in EGU/g is measured according to the following procedure:

A substrate solution containing 34.0 g/l CMC (Hercules 7 LFD) in 0.1M phosphate buffer at pH of 6.0 is prepared. The enzyme sample to be analyzed is dissolved in the same buffer. Ten ml substrate solution and 0.5 ml enzyme are mixed and transferred to a vibration viscosimeter (e.g. MIVI 3000 from Sofraser, France), and then thermostated at 40° C. One EGU is defined as the amount of enzyme that reduces the viscosity to one half under these conditions.

The above procedure is described in Analytical Method AF 275/1-GB which is available upon request from Novo Nordisk A/S. AF 275/1-GB is incorporated herein by reference.

The initial step must include a sufficient holding period. However, a rinsing step, a step with excessive heat or a step which has incompatible chemicals, e.g., oxidizing or bleaching agents, cannot follow the initial treatment until the incubation period is completed.

A sufficient holding time for the initial step ranges from one minute to 72 hours, preferably 30 minutes to 15 hours, and most preferably 2 hours to 12 hours, depending on the enzyme dosage, type of fabric and temperature. For example, a holding time for the initial treatment can be 30–40 minutes at 60° C. The holding time can also be 18 hours at about 30° C., however, a significantly lower dose should be applied.

The initial enzymatic treatment can be applied at various processing steps where suitable conditions exist, e.g., temperature and pH. Thus, the process according to the present invention can be adopted and optimized in practically any textile manufacturing process. For example, the initial treatment can be made in the latter processing steps. Preferably, the initial cellulase treatment is made before the finishing sequence.

In particular, the process may advantageously be practiced by subjecting a fabric to a first cellulase treatment, followed by cutting and sewing of the fabric into a garment and subjecting the garment to a second cellulase treatment. Each step may be performed either as a batch process or as a continuous process. Preferably, the first step is performed as a continuous process, whereas the second step may be performed as a batch process.

In a specific embodiment, the invention provides a process for treating a cellulosic fabric, which fabric has previously been treated with a cellulase to achieve a weight loss between about 0.05 and about 10.0% of the weight of the fabric, the process comprising an additional treatment of the fabric with a cellulase to achieve a further weight loss between about 0.05 and about 10.0% of the weight of the fabric. In particular, the cellulosic fabric may be a garment.

In the process according to the present invention, the first cellulase treatment of the fabric is followed by a second cellulase treatment. The second enzymatic treatment should result in a weight loss between about 0.05 and about 10.0%, preferably between about 0.05 and about 5.0%, more preferably between about 0.1 and about 2.5%, and most preferably between about 0.2 and about 2.0%, of the weight of the cellulosic fabric after the first treatment.

This weight loss in the second enzymatic treatment can be achieved by a dosage of between about 100 and about 40,000 EGU/kg of fabric, preferably between about 200 and about 20,000 EGU/kg of fabric.

A sufficient holding period for the second cellulase treatment is between 1 minute and 15 hours, preferably between 30 minutes and 12 hours, depending on the enzyme dosage, type of fabric and temperature.

It should be noted that additional enzymatic treatments may be applied between the first step and second step as needed to complete the biopolishing.

The cellulase treatment according to the present invention can be utilized in continuous textile manufacturing processes which, generally, have three stages, i.e., preparation, dyeing and finishing. In these processes, cellulase treatment usually takes place in the wet processing stages which encompasses desizing, scouring, bleaching, washing, dyeing and finishing.

The second cellulase treatment can be made immediately prior to drying without inducing the yellowing during drying that may be caused with higher dosages. The second step should be made as close to the end of the processing as possible. However, the continuous process must contain a final step which deactivates the enzyme. In a preferred embodiment, the cellulytic enzyme is inactivated between the first cellulase treatment and the second cellulase treatment.

Inactivation of cellulytic enzymes can take place in various ways. For example, inactivation occurs if the temperature or pH is elevated to a certain level for a certain period, depending on the thermostability or the pH tolerance of the enzyme employed. Certain aggressive agents, e.g., bleaching agents, may also inactivate enzymes.

In order to obtain the desired Bio-Polishing effects, it is known that enzymatic treatment also requires sufficient mechanical treatment. Mechanical treatment may occur during wet processing, e.g., during scouring, bleaching, washing, dyeing and finishing. Mechanical action may be caused by tumbling, by passing the fabric over rollers or cylinders, by pulling, tugging or stretching the fabric or by blasting or sparging the fabric.

The dosage of the cellulase in each treatment depends on the enzyme incubation time, i.e., a relatively short enzymatic reaction time necessitates a relatively increased enzyme dosage, and vice versa. In general, enzyme dosage may be stipulated in accordance with the reaction time available.

The process according to the present invention can be used to treat cellulosic yarns or materials. The materials may be woven or knitted, and may be made of cellulosic fibers, e.g., cotton, cotton/polyester blends, rayon, e.g., viscose, viscose/polyester blends, flax (linen) and ramie or other fabrics containing cellulose fibers. In particular, the cellulosic material may be rayon, e.g., viscose or cuprammonium, preferably the Lyocel product Tencel® (Courtaulds Fibers, Inc.). Woven and knitted fabrics can be processed in either rope or open-width form. An example of a cellulosic fabric may be a towel.

Cellulytic enzymes are well known. Preferred cellulytic enzymes are cellulases derived from fungi belonging to the genera Humicola, e.g., *H. lanuginosa, H. insolens* or *H. grisea* var. *thermoidea;* Trichoderma, e.g., *T. viride* or *T. longibrachiatum;* Myrothecium, e.g., *M. verrucaria;* Aspergillus, e.g., *A. niger* or *A. oryzae;* Botrytis, e.g., *B. cinerea;* or cellulases derived from bacteria belonging to the genera Bacillus; Cellulomonas; Aeromonas: Streptomyces; Actinomyces; or Hymenomycetes.

The cellulases can be obtained by recombinant DNA techniques by inserting the DNA sequence encoding the enzyme into an appropriate expression vector. A variety of host-vector systems may be utilized to express the DNA sequence encoding the enzyme.

Commercially available cellulase products include Cellusoft L™ and Denimax L™, supplied by Novo Nordisk A/S, Denmark. Cellusoft L™ and Denimax L™ contain a cellulase derived from *Trichoderma viride* and *Humicola insolens*, respectively.

Other cellulases which can be utilized in the process according to the present invention are endoglucanases. A specific endoglucanase which can be utilized is the cellulase preparation comprising a highly purified endoglucanase derived from *Humicola insolens*. DSM 1800 which was deposited on Oct. 1, 1981 at the Deutsche Sammlung von Mikroorganismen, Mascheroder Weg 1B. D-3300 Braunschweig, FRG, in accordance with the provisions of the Budapest Treaty. This cellulase preparation is described in Published PCT Application WO 91/17243 which is incorporated herein by reference. As stated therein, the molecular weight of the highly purified endoglucanase is about 43 kD as determined by SDS polyacrylamide gel electrophoresis and the isoelectric point is about 5.1 as determined by isoelectric focusing with marker proteins.

It should be noted that the cellulase used for the second step may be different from that used in the initial step.

The performance of cellulytic enzymes depends on process conditions such as pH and temperature. In accomplishing the process of this invention, factors such as pH-dependent performance and thermal stability should be taken into consideration in the choice of cellulytic enzymes. Preferably, the temperature in the cellulase treatments is between about 10 and 65° C. and the pH is between about 4 and about 9.5.

For Cellusoft L™, the pH should be in the range of about 4–6, for Denimax L™, the pH should be between about 6 and 8 and for the cellulase preparation comprising a highly purified endoglucanase derived from *Humicola insolens*, DSM 1800, the pH should be between about 5.5 and 9.5. The optimum temperature for all three cellulase preparations is between about 50 and 60° C. However, lower temperatures can be used by increasing the incubation time.

Wetting agents may also be used in the process according to the present invention. Preferred wetting agents are nonionic ethoxylated alcohols. Other chemicals which are presently used in the textile industry, e.g., buffers and other enzymes, may be used in combination with the cellulase, as long as the chemicals do not deactivate the cellulase and it is possible to run the process at a pH where the cellulase is active. These chemicals include dyestuffs, salts, e.g., sodium sulfate or chloride, and amylases.

It has surprisingly been found that the process according to the present invention provides additional pilling reduction than a single enzyme dosage. Moreover, the process according to the present invention allows for the removal of any additional yarns fibrillation that develops in processing following the initial treatment. Finally, "yellowing" of the cellulose fabric during drying is avoided by the process according to the present invention.

These results are illustrated in the following example which should not be construed to limit the scope of the present invention. Indeed, various modifications of the invention in addition to those shown and described herein will become apparent to persons skilled in the art from the specification. Such modifications are intended to fall within the scope of the appended claims.

EXAMPLE

Towel samples 30×30 cm were washed twice and then dried in a tumbler. The weight of the towels was measured after drying.

Most of the towels were treated with one of three cellulase preparations, Cellusoft L™, Denimax L™ or the cellulase preparation described in Published PCT Patent Application WO 91/17243 (hereinafter "endoglucanase"). The cellulase preparations were applied to the towels at either the Single Dose or the First Dose of the Two Step Cellulase Treatment provided in Table 1.

TABLE 1

Cellulase Preparations Used and Activities in EGU/g Enzyme Preparation

| | | Dosage (on weight of fabric) | | |
|---|---|---|---|---|
| | EGU/g | Single | First | Second |
| Cellusoft L ™ | 900 | 0.4% | 0.30% | 0.10% |
| Denimax L ™ | 104 | 3.0% | 2.25% | 0.75% |
| endoglucanase | 24 | 2.7% | 2.00% | 0.70% |

The cellulase treatment was performed in a Pad Batch Model with a wet pick-up of 115%. The towels were padded at room temperature and incubated for 2 hours at 55° C. The buffers provided in Table 2 were applied to the pad liquor to maintain the pH close to optimal.

TABLE 2

| | Buffer | pH |
|---|---|---|
| Cellusoft L ™ | 1.85 g/l CH$_3$COONa adjusted to pH 4.8 with CH$_3$COOH | 4.8 |
| Denimax L ™ and endoglucanase | 1.55 g/l NaH$_2$PO$_4$ 0.75 g/l Na$_2$HPO$_4$ | 7.0 |

After the cellulase treatment, the towel samples were washed twice in a washing machine prior to drying. The weight of the towels was measured and the total weight loss by cellulase and mechanical treatment was calculated in percent.

The towels which were treated with the First Dose of the Two Step Cellulase Treatment were treated again according to the above procedure with the appropriate Second Dose of the Two Step Cellulase Treatment provided in Table 1 above. The weight of the towels was measured again after the second cellulase treatment and the total weight loss by cellulase and mechanical treatment was calculated in percent.

The weight loss caused solely by mechanical treatment was determined using the following procedure. Two towels were incubated with only buffer, i.e., no cellulase was applied. The towels were subjected to the same mechanical treatment as the towels which were treated with the two step cellulase treatment: The weight loss of the fabric due solely to mechanical treatment was determined to be:

| 1. Single Dose and First Dose of the Two Step Cellulase Treatment: | 2.41% |
|---|---|
| 2. Second Dose of the Two Step Cellulase Treatment: | 1.40% |

The above experiment was carried out twice. The average weight loss in percent (as defined at page 3 above) of the cellulase-treated towels in the two runs is provided in Table 3.

TABLE 3

| | Cellusoft L ™ | Denimax L ™ | endoglucanase |
|---|---|---|---|
| Single Dose | 1.99 | 1.77 | 0.88 |
| First Dose | 1.59 | 1.36 | 0.32 |
| Second Dose | 1.21 | 1.24 | 0.69 |
| Total | 2.80 | 2.60 | 1.01 |

The results show that a two step cellulase treatment results in a significantly higher weight loss than a single dose treatment when the same total dose of cellulase is applied. Thus, cellulose fabrics treated with a two step cellulase treatment will have significantly less pilling and fuzz.

Furthermore, the results show that the two step cellulase treatment according to the present invention can achieve the same effect as a single dose application by applying a lower total dose of cellulases. Thus, the process according to the present invention is more cost effective than a single dose treatment.

We claim:

1. A process for manufacturing a cellulosic fabric comprising preparing, dyeing and finishing the cellulosic fabric, wherein said process further comprises the following sequential steps during the preparing, dyeing or finishing of the cellulosic fabric:
   (a) a first treatment of the cellulosic fabric with an amount of a first cellulase to achieve a weight loss between about 0.05 and about 10.0% of the weight of the fabric;
   (b) inactivation of the first cellulase; and
   (c) a second treatment of the cellulosic fabric with an amount of a second cellulase to achieve a weight loss between about 0.05 and about 10.0% of the weight of the fabric after step (a),
   wherein the combined weight loss obtained by the first and second treatments is greater than the weight loss obtained by a single treatment of the cellulosic fabric with the amounts of the first and second cellulase used in the first and second treatments, respectively.

2. The process according to claim 1, wherein the first treatment achieves a weight loss between about 0.5 and about 8.0% of the weight of the cellulosic fabric.

3. The process according to claim 2, wherein the first treatment achieves a weight loss between about 1.0 and about 5.0% of the weight of the cellulosic fabric.

4. The process according to claim 1, wherein the second treatment achieves a weight loss between about 0.05 and about 5.0% of the weight of the cellulosic fabric after step (a).

5. The process according to claim 4, wherein the second treatment achieves a weight loss between about 0.1 and about 2.5% of the weight of the cellulosic fabric after the first treatment.

6. The process according to claim 5, wherein the second treatment achieves a weight loss between about 0.2 and about 2.0% of the weight of the cellulosic fabric after the first treatment.

7. The process according to claim 1, wherein the first cellulase and/or the second cellulase is obtained from fungi belonging to the genera Humicola, Trichoderma, Myrothecium, Aspergillus or Botrytis.

8. The process according to claim 7, wherein the first cellulase and/or the second cellulase is obtained from fungi belonging to the species *H. lanuginosa, H. insolens, H. grisea* var. *thermoidea, T. viride, T. longibrachiatum, M. verrucaria, A. niger, A. oryzae* or *B. cinerea*.

9. The process according to claim 1, wherein the first cellulase and/or the second cellulase is obtained from bacteria belonging to the genera Bacillus, Cellulomonas, Aeromonas, Streptomyces, Actinomyces or Hymenomycetes.

10. The process according to claim 1, wherein the first cellulose and/or the second cellulase is an endoglucanase.

11. The process according to claim 10, wherein the endoglucanase is derived from *Humicola insolens*, DSM 1800.

12. The process according to claim 1, wherein the cellulosic fabric is a towel.

13. The process according to claim 1, wherein the cellulosic fabric is rayon.

14. The process according to claim 13, wherein the cellulosic fabric is cuprammonium.

15. The process according to claim 1, wherein the cellulosic fabric is a lyocel product.

16. The process according to claim 1, wherein the cellulosic fabric is viscose.

17. The process according to claim 1, wherein the pH in each treatment is between about 4 and about 9.5.

18. The process according to claim 1, wherein the temperature in each treatment is between about 10 and about 65° C.

19. The process according to claim 1, wherein the enzyme dosage in the first treatment is between about 100 and about 40,000 EGU/kg of the cellulosic fabric.

20. The process according to claim 19, wherein the enzyme dosage in the first treatment is between about 200 and about 20,000 EGU/kg of the cellulosic fabric.

21. The process according to claim 1, wherein the enzyme dosage in the second treatment is between about 100 and about 40,000 EGU/kg of the cellulosic fabric.

22. The process according to claim 21, wherein the enzyme dosage in the second treatment is between about 200 and about 20,000 EGU/kg of the cellulosic fabric.

23. The process according to claim 1, wherein the incubation time for each treatment is between one minute and 72 hours.

24. The process according to claim 1, wherein the cellulase is genetically engineered.

25. The process according to claim 1, further comprising cutting and sowing the cellulosic fabric into a garment after the first treatment but prior to the second treatment.

26. The process according to claim 1, wherein both treatments are conducted as continuous processes.

27. The process according to claim 1, wherein both treatments are conducted as batch steps.

28. The process according to claim 1, wherein the first treatment is conducted as a continuous process and the second treatment is conducted as a batch step.

29. The process according to claim 1, wherein the first treatment is made prior to the finishing stage.

* * * * *